US005710101A

United States Patent [19]

Carstairs et al.

[11] Patent Number: 5,710,101
[45] Date of Patent: Jan. 20, 1998

[54] COMPOSITION FOR TREATMENT OF PLANT MATERIAL COMPRISING AN AMINOPURINE AND A SULFONATED POLYESTER OR SULFONAMIDE

[75] Inventors: Margaret Louise Carstairs, Anstruther; Laurence William Irvine Jennings, Pittenweem, both of Scotland

[73] Assignee: British Technology Group Ltd., London, England

[21] Appl. No.: 545,680

[22] PCT Filed: Apr. 29, 1994

[86] PCT No.: PCT/GB94/00924

§ 371 Date: Jan. 11, 1996

§ 102(e) Date: Jan. 11, 1996

[87] PCT Pub. No.: WO94/24856

PCT Pub. Date: Nov. 10, 1994

[30] Foreign Application Priority Data

May 1, 1993 [GB] United Kingdom ............... 9309095
Aug. 17, 1993 [GB] United Kingdom ............... 9317063

[51] Int. Cl.$^6$ .................................................. A01N 3/02
[52] U.S. Cl. .................. 504/115; 504/136; 800/DIG. 67
[58] Field of Search ........................ 504/115, 136; 426/615; 800/DIG. 67

[56] References Cited

U.S. PATENT DOCUMENTS 3,112,192   11/1963   Feichtmtmeir et al. ............... 71/2.5
4,594,092    6/1986   Speltz et al. ............................. 71/77
5,112,380    5/1992   Yamamoto et al. ...................... 71/68

FOREIGN PATENT DOCUMENTS 761872    6/1967   Canada .
854560   11/1960   United Kingdom .

OTHER PUBLICATIONS

Chemical Patents Index, Documentation Abstracts Journal, Section Ch, Week 9223, Derwent Publications Ltd., London, GB, Class C, AN 187699, & JP A 4,117,301(Kureha Chem Ind Co Ltd) 17 Apr. 1992, see abstract.

Chemical Patents Index, Documentation Abstracts Journal, Section Ch, Week 9332, Derwent Publications Ltd., London, GB, Class C, AN 252568 & JP A 63,181,93313 (Kyoeah Hakko Kogyo Co.) Oct. 1993, see abstract.

Central Patents Index, Basic Abstracts Journal, Section Ch, Week 6700, Derwent Publications Ltd., London, GB, Class C, AN 9647G & CA A,761,872 (Kelco Co), see Abstract.

Central Patents Index, Basic Abstracts Journal, Section Ch, Week 7023, Derwent Publications Ltd., London, GB, Class C, AN 41584R & JP A,7,016,054 (Mikasa Kagaku Kogyo KK), 4 Jun. 1970., see Abstract.

*Primary Examiner*—S. Mark Clardy
*Attorney, Agent, or Firm*—Nixon & Vanderhye

[57] ABSTRACT

The invention provides a composition for sustaining plant material comprising an aminopurine or a derivative or salt thereof and at least one water soluble sulfonated polyester or sulfonamide.

12 Claims, No Drawings

COMPOSITION FOR TREATMENT OF PLANT MATERIAL COMPRISING AN AMINOPURINE AND A SULFONATED POLYESTER OR SULFONAMIDE

This application has been filed under 35USC371 as a national stage application of PCT/GB94/00924, filed Apr. 29, 1994.

The present invention is concerned with the sustenance of plant material, for example cut flowers, and plants.

After harvesting, plant material remains alive although death will begin to occur after a delay, mainly due to lack of water and essential nutrients. The plant material will begin to perish immediately following harvesting and deterioration may be very rapid indeed, depending on the particular plant material in question and the surrounding conditions (e.g. heat, humidity, etc.). For example, picked flowers may be noticeably wilted only minutes after the time of picking.

To prevent such rapid deterioration in their condition, cut flowers or foliage are generally placed with their stems extending into water. It is also conventional for sugars, such as glucose, to be added to the water to further maintain the cut plant material in a visually acceptable form.

Where the harvested plant material must be transported or stored for long periods of time, the maintenance of the plant matter in an acceptable condition is more problematic. It is usual for the plant matter to be chilled and maintained at temperatures between 1° C. and 8° C. The decreased temperature depresses the rate of metabolism in the plant cells thus delaying cell death and spoilage of the plant material as a whole. However, maintenance of low temperatures continually throughout transportation or storage is inevitably expensive and further the plant material may itself be distressed or even injured by exposure to such temperatures, especially where the exposure is prolonged. A further problem connected to cold storage or chilling of plant matter is the continuing vulnerability to attack by cryophilic bacteria or fungi.

A similar problem may also occur in the transport or storage of rooted plants, for example pot plants. Although these plants are generally more robust than cut plant material and are generally less stressed it is none the less desirable that the plants are healthy and attractive when offered for retail despite undergoing long periods of transport and/or storage. Thus, for example, it is generally recognised to be advantageous if any flowering plants are in bloom in an attractive manner. The problem encountered here, however, is maintaining the plant in the required state during transport or storage.

The present invention provides a composition which sustains plant material. In particular, the present invention provides a composition for sustaining plant material comprising an aminopurine or a derivative or salt thereof and at least one component selected from the group consisting of a water soluble polymer and a water soluble compound containing a sulphonyl group.

The word "sustains" is used herein to mean that the treated plant material is maintained in whatever state it is in at the time of application of the composition for a relatively long time compared to untreated plant material.

Thus, for example, if the composition is applied to cut flowers picked in bud, the flowers will remain unopened for up to two months after application of the composition. By comparison, untreated flowers will bloom and die in a much shorter time. Likewise, the composition according to the invention may be applied to pot plants, maintaining them In bud for several weeks, The composition of the present invention is effective at sustaining plant material at temperatures of up to 30° C., preferably 2° C. to 18° C., more preferably 5° C. to 15° C. Within this range it is preferred that the plant material is maintained at temperatures of 8° C. and above, for example 8° C. to 12° C., in order to avoid stressing the plant material by chilling.

According to one aspect of the present invention there is provided a composition comprising an aminopurine or a derivative or salt therof and a water-soluble polymer. This composition, which is preferably aqueous, may be used to sustain plant material retarding the normal course of plant development or decay.

Advantageously, the aminopurine may be 6-furfurylaminopurine (also known as Kinetin) which is a known plant hormone. Kinetin is practically insoluble in water and is reported to be a plant growth promoter at low concentrations. In very high concentrations, for example 200 mg/liter and above, Kinetin has been noted to have a retardation effect on plant growth. However, the difficulties of producing the highly concentrated solutions of Kinetin required to produce a retardation effect in plant growth and the high cost of Kinetin have combined to make this approach commercially non-viable.

A further problem regarding the use of Kinetin is that when dissolved in water (following pre-dissolution in another suitable solvent) the Kinetin solutions must be stored at below 0° C. or the material will crystallise out.

Other aminopurines can be used in the composition according to the present invention and suitable examples include adenine, 6-benzylaminopurine, N-benzyl-9-(2-tetrahydropyranyl)adenine, N-(2-chloro-4-pyridyl)-n-phenylurea, diphenylurea, 6-($\gamma$,$\gamma$-dimethyl-allylamino) purine, 1-phenyl-3-(1,2,3-thiadiazol-5-yl)urea adenine hemi-sulphate and (6-(4-hydroxy-3-methyl-but-2-enylamino)purine).

Conveniently, the composition according to the present invention in dilute, ready-to-use form comprises 0.5 to 20 mg/liters, preferably 2 to 10 mg/liter and especially preferably 4.0 to 8.0 mg/liter of an aminopurine, such as Kinetin.

The effect of the aminopurine on plant growth is synergistically enhanced by the presence of the water-soluble polymer. Thus, the present invention also provides a composition containing synergistically effective amounts of an aminopurine (or a derivative or salt thereof) and a water-soluble polymer.

Any water-soluble polymer is effective in the present invention and mention may be made of water-soluble starches, starch derivatives, amylose, celluloses and cellulose derivatives, for example carboxymethylcellulose, methylcellulose, hydroxyethylcellulose, methylhydroxyethylcellulose, methylhydroxypropylcellulose and monochloroacetocarboxymethyl-cellulose. Conveniently, the water-soluble polymers are present as salts with suitable cations, for example as their sodium or potassium salts.

In one preferred aspect, the present invention provides a composition to sustain plant material, said composition comprising 6-furfurylaminopurine and carboxymethylcellulose or a salt thereof.

Whilst we do not wish to be bound by theoretical considerations, it is believed that the compositions of the present invention mimic the conditions experienced by hormonal chemicals, such as Kinetin, inside plant cells or in the xylem of plants by providing an environment containing polymers equivalent to the cellulose or ligno-cellulose naturally present.

Instead of, or in addition to, a water-soluble polymer the composition of the present invention may comprise a water soluble compound containing a sulphonyl group, such as a polyester. Sulphonated polyesters may be used in this regard. Also suitable for use in the compositions of the invention are the group of polyesters found in plants which have a "tannin-like" structure and which are conventionally used as preservatives in leather tanning. Generally, these polyesters have benzyl groups alternating with glycerol. A particularly preferred polyester is the sulphonated polyester formed from pentaerythritol and phthallic anhydride whose preparation is described in Example 1 hereinafter. For convenience, this will be referred to as polysulphono-di-pentaepythrityl-1,2-benzene-di-carboxylate. Alternatively, the compound containing a sulphonyl group may be a sulphonamide, such as sulphanilamide. Other Sulphonamides of the general formula $H_2N$—$C_6H_4$—$SO_2$—$NHR$ where R represents a variety of chemical groups are also of interest. Sulphonamide drugs in which R is a substituted pyrimidine group are of particular interest.

Thus, the present invention also provides a composition comprising an aminopurine or a derivative or salt thereof and a water soluble compound containing a sulphonyl group, such as a water-soluble ester, sulphanilamide or other sulphonamide. This composition, which is preferably aqueous, may be used to sustain plant material retarding the normal course of plant development or decay. In another aspect the present invention also provides a composition containing synergistically effective amounts of an aminopurine (or a derivative or salt thereof) and a compound containing a sulphonyl group, such as a water-soluble ester, sulphanilamide or other sulphonamide.

In one preferred aspect, the present invention provides a composition to sustain plant material, said composition comprising 6-furfurylaminopurine and polysulphono-di-pentaerythrityl-1,2-benzene-di-carboxylate or salts thereof.

In a further preferred aspect, the present invention provides a composition for sustaining plant material comprising 6-furfurylaminopurine and a sulphonamide, preferably sulphanilamide.

A synergistic effect is observed in the effectiveness of the composition when the water soluble compound containing a sulphonyl group, such as a polyester, sulphanilamide or other sulphonamide, is present together with the water-soluble polymer and a composition comprising an aminopurine together with both water-soluble polymer and a water soluble compound containing a sulphonyl group, such as a water-soluble ester, sulphanilamide or other sulphonamide, forms a further aspect of the invention.

Optionally the composition may also include other additives such as, for example, a colour stabiliser such as caffeine, vitamin substrates such as myo-inositol, antibiotics such as penicillin, agents to control bacterial growth such as sodium metabisulphite, a fungicide such as carbendazim or a yeast inhibitor such as undecanoic acid or Nystatin.

To maintain a proper nutrient balance the composition may also include nitrogen and phosphorus containing compounds, such as nitrates and ammoniacal nitrogen or phosphates, as well as sugars, calcium and potassium salts.

Buffers and other conventional additives may also be included in the composition. In particular, the pH of the solution may be adjusted to be pH 3.0–8.0, preferably slightly acidic (pH 3.0–5.5) to mimic the pH of sap. Acids such as acetic acid, citric acid, propionic acid, tartaric acid and lactic acid may be useful in this regard. Mention may also be made of sodium acetate, calcium gluconate, calcium tactate, potassium sodium tartarate and potassium hydrogen phosphate as being suitable buffers. Zwitterions such as naturally occurring amine acids (e.g. glycine) may also be used to control the pH.

It is especially desirable that metals heavier than aluminum are not present in the composition of the present invention. In this regard chelating agents, such as EDTA (ethylenediamine-tetraacetic acid) or DTPA (diethylenetriaminepentaacetic acid) may be added to remove any contaminating heavy metals which may be present in the water making up the composition.

Osmotic pressure regulators may also be included in the solution. Examples of suitable regulators include glucose, glucose hydrates such as mannitol and serbitol, sucrose, fructose, trioses such as maltotriose, polyols such as pentaerythritol, or derivatives or mixtures thereof.

The composition according to the present Invention may be produced either as an aqueous solution which is ready for application to the plant material, or as a concentrate in either liquid or solid form. The concentrate may be diluted with water prior to application or may be used to "top up" existing solutions on a continuous production basis. Where a concentrate is produced, a complex in the form of a micro-crystalline precipitate is produced which can be readily dissolved in water, prior to use. When the composition is in the form of a concentrate, the Kinetin is preferably present in an amount from 0.005 to 0.70%, preferably 0.01 to 0.60%, by weight, the water soluble polymer (if present) is present in an amount from 8 to 96%, preferably 10 to 95%, by weight and the water soluble compound containing a sulphonyl group (if present) is present in an amount from 2–85%, prefrably 4–80%, by weight. When the composition is in dilute, ready-to-use form, the Kinetin is preferably present in an amount from 0.5 to 20 ppm, preferably 2 to 10 ppm and especially 4 to 8 ppm, the water soluble polymer (if present) is present in an amount from 50 to 25000 ppm, preferably 100 to 20000 ppm, and the water soluble compound containing a sulphonyl group (if present) is present in an amount from 200–2500 ppm. preferably 300 to 2000 ppm.

The aqueous solution which is produced either directly or as a dilution of a previously prepared concentrate may be applied to the plant material either by placing the cut stems in a container which is charged with a portion of the aqueous composition, preferably filled with the aqueous composition to a depth of up to halfway to two-thirds of the stem (depending on the foliage cover), or alternatively, the composition may be sprayed directly onto the surface of the plant material. The technique of spraying the composition onto the plant surface is of particular utility for plants which are rooted in soil. This is due to the fact that the soil particles tend to absorb the composition which consequently fails to reach the root system of the plant in the required quantities. Spraying the foliage of a rooted plant allows the composition to be absorbed through the cells. It is generally desirable to spray a rooted plant with the composition more than once, for example 2 to 5 times, allowing absorption of the composition between each spraying.

Where the plant material has been cut or where the root system of a plant is free from soil particles, absorption of the composition may be by absorption through the roots or stem. Cut plants may also be sprayed as an alternative to, or in addition to, uptake of the composition through the stem.

Once the period of transportation or storage is complete and it is desired that the plant should now continue to develop normally the effects of the composition can be countermanded by simple washing in water. Clearly, where the plant material has been sprayed with the composition, removal must be by immersion or, more preferably, by spraying the treated surfaces with water. If desired, in the case of harvested plant material, the treated plant material may be transferred to the composition for promoting the continued development of harvested plant material described in applicant's co-pending patent application which claims priority from British patent applications nos. 9309095.9 and 9311061.1. In this case, it is not essential to wash the plants prior to transferral although this may be desirable.

It is envisaged that plant material may be transported or stored whilst constantly immersed in the composition of the invention. For instance, this may be accomplished by means of an aquapack or a suitable consumer display unit. However, it has been found to be advantageous in terms of overall plant life to immerse the plant material in the composition of the invention for a specified period of time and then transfer the plant material to a dry pack for transportation or storage. Consequently, in one particularly preferred embodiment, sufficient composition is applied to the plant material so that after removal and drying of the treated surfaces, the delaying effect of the development of the plant material continues. Thus, cut flowers may be treated with the composition by Immersion of their stems, as described above, and once the cut flowers are sufficiently treated, they can be removed from the composition, dried and stored or transported without further need for the presence of water. Generally, it is desirable that where the flowers are to be transported dry a higher concentration of water-soluble polymer is present in the composition used for treatment.

The present invention is of particular application to cut flowers and foliage. Where flowers are to be treated, better effects may be obtained if the flowers are treated whilst in bud, especially if the flowers are treated whilst still in tight bud.

The composition can be used for any type of plant material, especially commercial and garden flowers, shrubs, foliage, etc. The composition is particularly useful for cut flowers, especially roses, irises, carnations, lilies, daffodils, sweet peas, freesias, poppies, orchids, chrysanthemums and soft-stemmed flowers such as anemones, phlox and sweet williams, foliage such as lilac and eucalyptus, and Christmas trees.

A particular problem occurs in the storage of cut roses, which frequently wilt quickly despite immediate transfer to an adequate supply of water. It has now been found that if the end of a freshly cut rose stem is chemically cleaned, for example in alcohol such as isopropanol, the life of the cut rose is considerably extended and this forms a further aspect of the present invention. It is believed that cleaning the rose stem in this manner removes oils which seep from the cells damaged by the cutting process and which then block the phloem and/or xylem of the cut rose.

Once treated, the plant material is delayed in developing further. However, the plant material cannot be maintained indefinitely simply by treatment with the composition of the invention and, if the treated plant material is simply left too long, death will eventually result.

The present invention further provides a method for delaying normal plant development, this method comprising the application of a composition, as described above, to plant material. Where the plant material is cut roses, the method may optionally comprise a preliminary step of cleaning the cut rose with alcohol.

In a further aspect, the present invention provides plant material, for example cut flowers, treated with the composition referred to above.

Viewed from another aspect, the present invention provides the use of an aminopurine, such as Kinetin, or a composition as defined above to retard the development of plant material, in particular cut flowers and/or foliage.

The invention is further described by the following, non-limiting examples:

EXAMPLE 1

Preparation of sulphonated polyester (polysulphono-di-pentaerythrityl-1,2-benzenedicarboxylate pentaerythritol (27 g) was mixed with phthallic anhydride (15 g) and concentrated sulphuric acid (98% v/v, 20 ml) and the mixture was then heated to 135° C. and maintained thus for 20 minutes. On cooling, the mixture was brought to just alkaline with sodium hydroxide solution (40% w/v, 60 ml). On cooling to room temperature, the clear brown-yellow liquid was filtered at the pump and set to evaporate to near dryness in an oven at 100° C. overnight. The reduced filtrate was extracted twice with methanol (250 ml), heated to 60° C., filtered and the methanol then recovered by distillation. The residue from the distillation was dried in the oven at 100° C. overnight to yield a brown-yellow glass (about 24 g) which was mobile at 300° C. and solid at room temperature.

Characterisation

| I.R. Spectrum: | |
| --- | --- |
| Band Frequency | Interpretation |
| 810 cm$^{-1}$ | di-substituted ring |
| 1000 cm$^{-1}$ | C—O stretch (Ester) |
| 1250 cm$^{-1}$ | C—O stretch (Ester) |
| 1560 cm$^{-1}$ | ring vibrations |
| 1715 cm$^{-1}$ | C=O stretch (Ester) |
| 2850 cm$^{-1}$ | C—H ring |
| 3300 cm$^{-1}$ | —OH (Alcohol) |

EXAMPLE 2

A solution of 6-furfurylaminopurine (Kinetin) was prepared by weighing an amount of 20 to 200 mg into a flask and adding NaOH solution (2–4 mg solution) and shaking to dissolve. This solution was rapidly diluted to approximately 100 ml with water. Next, a solution of carboxymethyl cellulose (CMC) (low viscosity Grade 7ULC) was prepared using 10 g to 15 g in 100 ml of water. The Kinetin and CMC solutions were mixed together.

A chosen polyester was added in an amount of 5 g to 15 g. In this preferred embodiment, the chosen polyester was polysulphono-di-pentaerythrityl-1,2-benzenedicarboxylate prepared as described in Example 1.

The remaining components were added. The nitrate, phosphate, ammoniacal nitrogen and potassium together were comprised in a solution prepared separately and yielding per ml 98.7 mg $NO_3$, 55.0 mg $PO_4$, 50.7 mg $NH_4$, 30.0 mg $K^+$ (Potassium ions). This solution was added in a volume of between 10 ml to 20 ml.

Next, myo-inositol (1–2 g) was added and, finally, any chosen fungicide (e.g. approximately 0.2 g carbendazim), a bactericide such as sodium metabisulphite (e.g. 1 g–3 g), and a yeast inhibitor if required.

The whole composition was mixed together to yield the concentrate in a volume of about 220 ml which was used at a dilution of 11 ml per liter to yield the working fluid.

EXAMPLE 3

A liter Erlenmeyer flask was filled with test solution, formulated as shown below:

| | |
|---|---|
| Carboxymethylcellulose (7ULC) | 10 g |
| Kinetin | 0.005 g |
| (Stock Solution) | |
| Acetate ester of CMC | 1 g |
| Sodium chlorocyanurate | 0.2 g | in one liter of water.

Ten stems of roses were placed in the flask to a depth of 15 cm and then left at 10° C. for 24 hours. The flowers were then removed and placed in a bubble pack lined box. Two control flowers were similarly treated in Water alone. Treated roses were removed at two day intervals and placed into water containing plant food.

The first seven flowers removed recovered and bloomed normally.

The remaining three flowers did not recover. The maximum storage time was found, therefore, in this case to be fourteen days.

The control flowers, removed on days 2 and 4, both failed to recover.

EXAMPLE 4

The composition was formulated using:

| | |
|---|---|
| Carboxymethylcellulose (CMC) 7ULC | 20 g |
| Kinetin | 0.010 g |
| Sodium Chlorocyanurate | 0.3 g |
| Teepol (a surfactant) | 0.1 g |
| Sulphonated Polyester (prepared as described in Example 1) | 1.0 g | in one liter of water.

Fifteen Dianthus stems were conditioned overnight in coot water, then transferred to a flask charged with the test solution described above and allowed to stand in the liquid for 36 hours at 10° C. The blooms were then stored in a bubble pack lined box held at approximately 10° C.

Control

Two stems were placed directly In water and placed in a warm climate (23° C.), where they lasted for five days before senescing.

Stems were withdrawn from the bubble pack sequentially at two and three day intervals after one week in store. The stems were limp on withdrawal but found to condition normally and open fully when placed in water in a warm climate. The stems lasted as flowers for four or five days following reconditioning. The last stems, withdrawn after 30 days in storage lasted only two days, giving a maximum storage, in these conditions, of around 28 days.

The results are shown in Table 1.

TABLE 1

| Days | No. of Stems Transferred | Days to First Sign of Senescence | Days to Failure |
|---|---|---|---|
| 8 | 2 | 4 | 6 |
| 10 | 1 | 6 | 6 |
| 12 | 1 | 4 | 8 |
| 15 | 2 | 6 | 10 |
| 17 | 1 | 5 | 6 |
| 22 | 1 | 4 | 9 |

TABLE 1-continued

| Days | No. of Stems Transferred | Days to First Sign of Senescence | Days to Failure |
|---|---|---|---|
| 24 | 2 | 4 | 7 |
| 26 | 1 | 3 | 4 |
| 29 | 2 | 2 | 2 |

EXAMPLE 5

A composition was made by admixing together;

| | |
|---|---|
| Carboxymethyl Cellulose (CMC) 7ULC | 10 g |
| Water-soluble ester (prepared as described in Example 1) | 2 g |
| Kinetin | 0.0075 g |
| Sodium Chlorocyanurate | 0.3 g |
| Teepol | 0.1 ml | in one liter of water.

Twelve stems of a large bloomed variety of rose were placed in the composition formulated as described above, for a total of 28 hours at 12° C. The stems were placed in a bubble pack and double polythene lined box which was then flushed with $CO_2$ gas, morning and evening for the duration of the test.

Control

Two stems were taken for controls and these were placed in a warm climate. The control stems senesced in three days. One untreated stem kept in the box for five days failed to recover even after immersion in water.

Results

After five days, the treated roses were removed sequentially at one to three day intervals, reconditioned by immersion in water and set in a warm climate to bloom. On reconditioning, blooms lasted from 3 to 5 days except for the last bloom withdrawn which failed to recover after two days, giving a maximum storage time of 14 days under these conditions. The results are summarised in Table 2.

TABLE 2

| Days after treatment | No. of Treated Flowers Removed and conditioned | Lifetime after Conditioning (Days) |
|---|---|---|
| 5 | 1 | 4 |
| 6 | 2 | 5 |
| 7 | 1 | * |
| 10 | 1 | 3 |
| 12 | 1 | 5 |
| 14 | 2 | 4 |
| 17 | 1 | 2 |

*Stem broken; no result.

NB "Conditioning"=immersion in water

EXAMPLE 6

Samples of polygonatum (Solomon's Seal) were harvested in light bud and set in flasks, each charged with 500 ml of the working solutions.

It had been noted that solutions of water-soluble polyester prepared as described in Example 1 seemed to prevent leaf fall. Flasks were charged with water (Flask A), a solution containing 200 mg of Kinetin (Flask B) and a solution of 1 g/liter polyester (prepared as described in Example 1) and Kinetin (5 mg) (Flask C).

After a number of trials, the final experiment gave the following results after 14 days.

| WATER (Flask A) | WATER AND KINETIN (Flask B) | POLYESTER AND KINETIN (Flask C) |
|---|---|---|
| Plant dead | Plant still remarkably green some evidence of damage to florets | Plant similar in appearance to B, less damage to florets |

EXAMPLE 7

Forty-five stems of Iridace (Iris) in tight bud were split into three equal groups. Each group was placed in a flask and the flasks were maintained separately. One group (Group A) was held in just water, one group (Group D) was placed in test solution and, lastly, one group (Group C) was held in conditions believed to reflect current best practice (namely, the flowers were placed in water at a low temperature of around 5° C. containing "Chrysal"). The flowers were examined daily. The test was conducted in the absence of light for the first seven days. On day eight, the surviving blooms held in the test solution were transferred to a composition as defined in applicant's co-pending patent application which claims priority from British patent applications nos. 9309095.9 and g3170611 (Solution D). The test solution contained:

| | |
|---|---|
| Carboxymethylcellulose (7ULC) | 2 g |
| Kinetin | 0.005 g |
| Soluble Polyester (prepared as described in Example 1) | 2 g |
| Myo-inositol | 0.1 g |
| Sodium metabisulphite | 0.2 g |
| $KNO_3$ | 0.129 g |
| $(NH_4)_2 HPO_4$ | 0.129 g |
| Citric acid | 0.005 g | in one liter of water.

The results are shown in Table 3 below. In this table, the expression "damped off" means "rotting".

TABLE 3

| | NUMBER OF BLOOMS OPENED | | |
|---|---|---|---|
| DAY | 5° C. WATER + "CHRYSAL" BEST CURRENT PRACTICE (Group C) | 13° C. TEST SOLUTION (Group B) | 13° C. WATER (Group A) |
| 1 | 0 | 0 | 0 |
| 2 | 0 | 0 | 0 |
| 3 | 0 | 0 | Showing damage |
| 4 | All open | 0 | All damped off |
| 5 | All open | 1 | All damped off |
| 6 | All open | 1 | All damped off |
| 7 | Blooms curled at petal edges | 1 | All damped off |
| 8 | Blooms curled at petaled edges | Transferred to Solution D | All damped off |
| 9 | All damped off | All open | |
| 10 | | All open | |
| 11 | | All open | |

EXAMPLE 8

Two test solutions were prepared having the following compositions:

| Test Solution A (Constant Immersion) | |
|---|---|
| Kinetin | 0.2 g |
| Carboxymethylcellulose (7ULC) | 15.0 g |
| Sulphonated Polyester (prepared according to Example 1) | 15.0 g |
| Myo-inositol | 2.0 g |
| Sodium metabisulphite | 2.0 g |
| $KNO_3$ | 2.58 g |
| $(NH_4)_2 HPO_4$ | 2.14 g |
| made up to 20 liters in water | |

| Test Solution B (Timed Immersion) | |
|---|---|
| Kinetin | 0.2 g |
| Carboxymethylcellulose (7ULC) | 50.0 g |
| Sulphonated Polyester (prepared according to Example 1) | 10.0 g |
| Sodium metabisulphite | 2.0 g |
| $KNO_3$ | 2.58 g |
| $(NH_4)_2 HPO_4$ | 2.14 g |
| made up to 20 liters in water | |

Constant Immersion test

65 Lilies (Group 1) were placed in a vessel containing 1 liter of test solution A and 13 lilies (Control Group 1) were placed in a vessel containing 1 liter of water. The number of open blooms in each group was recorded initially and at daily intervals for 6 days.

Timed Immersion test

48 Lilies (Group 2) were placed in a vessel containing 1 liter of test solution B for 18 hours and then transferred to a dry pack box. Similarly, 14 lilies (Control Group 2) were placed in a vessel containing 1 liter of water for 16 hours and then transferred to a dry pack box. The number of open blooms in each group was recorded at daily intervals for 6 days.

The results are shown in Table 4 below.

TABLE 4

| | NUMBER OF OPEN BLOOMS ON EACH DAY | | | |
|---|---|---|---|---|
| DAY | GROUP 1 | CONTROL GROUP 1 | GROUP 2 | CONTROL GROUP 2 |
| 0 | 0 | 1 | | |
| 1 | 6 (~10%) | 4 (~30%) | 0 | |
| 2 | 12 | 5 | 1 | 4 |
| 3 | 17 (~25%) | 5 (~40%) | 4 | 7 |
| 4 | 37 | 7 | 10 | 8 |
| 5 | 50 (~75%) | 9 (~70%) | 14 | 12 |
| 6 | 57 (~85%) | 12 (~90%) | 18 (~40%) | 12 (~85%) |

NB The figures in parentheses indicate the approximate percentage of the total number of flowers which have open blooms.

Discussion

From the above results, it will be apparent that flowers will not last indefinitely under constant immersion conditions. For instance, for lilies, the maximum storage period under constant immersion conditions would appear to be around 6 days. However, if the flowers are treated under timed immersion conditions and then transferred to a dry pack, the maximum storage period would appear to increase.

For instance, for lilies, less than 40% of the flowers treated under timed immersion conditions had opened 6 days after treatment had commenced compared to more than 85% of the control groups and the group treated under constant immersion conditions.

EXAMPLE 9

Three rooted rose plants (Pink Peace) were examined and the longest growing shoot was measured and recorded for each rose plant. One rose plant was inverted and immersed to a depth covering the growing points in a test solution having the following composition:

| | |
|---|---|
| Kinetin | 0.004 g |
| Carboxymethylcellulose (7ULC) | 2.0 g |
| Sulphanilamide | 0.2 g |
| Hydroxyquinoline | 0.2 g |
| Diphenyl urea | 0.002 g | made up to 1 liter in water.

Two control rose plants were similarly immersed in water and one of these control plants (Control 1) was removed from the water and immersed in test solution part way through the test for a period of 24 hours before being removed and left in a dry place. All the plants were kept in a cabinet at 16° C. which was lit by a tungsten lamp for approximately 50% of the time. The length of the longest growing shoot was measured daily for each rose plant and the results are set out in Table 5 below.

TABLE 5

| | LENGTH OF LONGEST GROWING SHOOT (cm) | | |
|---|---|---|---|
| DAY | TEST SOLUTION | CONTROL 1 | CONTROL 2 |
| 0 | 5.0 | 5.0 | 5.7 |
| 1 | 5.4 | 8.0 | 9.0 |
| 2 | 5.5 | 9.5* | 11.0 |
| 3 | 6.8 | 9.5** | 13.3 |
| 4 | 8.0 | 9.5 | 16.2 |
| 5 | 8.0 | 9.5 | 17.0 |
| 6 | No check | No check | No check |
| 7 | 10.0 | 10.0 | 21.0 |
| 8 | 11.0 | 11.0 | 23.5 |
| 9 | 13.0 | 13.0 | 26.0 |
| 10 | 16.0 | 13.0 | 27.2 |

*indicates transferred to test solution
**indicates removed from test solution

We claim:

1. A composition for sustaining plant material comprising an aminopurine or a derivative or salt thereof and a water-soluble compound containing a sulphonyl group selected from the group consisting of a sulphonated polyester and a sulphonamide.

2. A composition according to claim 1, which further comprises a water-soluble polymer.

3. A composition according to claim 2, in which the water soluble polymer is carboxymethylcellulose or a salt thereof.

4. A composition according to claim 1, in which the aminopurine is 6-furfurylaminopurine (Kinetin).

5. A composition according to claim 1, in which the sulphonated polyester is the reaction product between pentaerythritol and phthallic anhydride.

6. A composition according to claim 5, wherein the pentaerythritol and phthallic anhydride are present in the ratio of 2:1.

7. A composition according to claim 1, in which the sulphonamide is sulphanilamide.

8. A composition according to claim 1, in the form of a ready-to-use aqueous solution.

9. A composition according to claim 1, in the form of a solid concentrate.

10. A composition according to claim 1, in the form of a liquid concentrate.

11. A method for delaying normal plant development which comprises treating plant material with a composition as defined in claim 1.

12. Plant material treated with a composition as defined in claim 1.

* * * * *

UNITED STATES PATENT AND TRADEMARK OFFICE
CERTIFICATE OF CORRECTION

PATENT NO. : 5,710,101
DATED : January 20, 1998
INVENTOR(S) : CARSTAIRS et al

It is certified that error appears in the above-identified patent and that said Letters Patent is hereby corrected as shown below:

Column 3, line 14, delete "pentaepythrityl" and replace by --pentaerythrityl-- ;

Column 3, line 67, delete "tactate" and replace by --lactate--.

Column 9, line 39, delete "0.129 g" opposite "$(NH_4)_2HPO_4$" and replace by --0.107 g--.

Signed and Sealed this

Fourteenth Day of April, 1998

Attest:

BRUCE LEHMAN

*Attesting Officer*  *Commissioner of Patents and Trademarks*